(12) United States Patent
Reboul (10) Patent No.: US 7,744,580 B2
(45) Date of Patent: Jun. 29, 2010

(54) DEVICE AND PROCEDURE FOR THE EXTEMPORANEOUS PREPARATION OF AN INDIVIDUAL QUANTITY OF STERILE LIQUID

(75) Inventor: Gerard Reboul, Toulouse (FR)

(73) Assignee: Arcadophta, Toulouse (FR)

( * ) Notice: Subject to any disclaimer, the term of this patent is extended or adjusted under 35 U.S.C. 154(b) by 1850 days.

(21) Appl. No.: 10/771,325

(22) Filed: Feb. 5, 2004

(65) Prior Publication Data

US 2004/0158204 A1    Aug. 12, 2004

Related U.S. Application Data

(60) Provisional application No. 60/444,977, filed on Feb. 5, 2003.

(30) Foreign Application Priority Data

Feb. 5, 2003    (FR)    ................................. 03 01334

(51) Int. Cl.
*A61B 19/00* (2006.01)
*A61M 5/178* (2006.01)

(52) U.S. Cl. ........................ 604/405; 604/403; 604/406; 604/407; 604/186

(58) Field of Classification Search ......... 604/403–416, 604/186, 199, 207, 217; 141/2
See application file for complete search history.

(56) References Cited

U.S. PATENT DOCUMENTS 3,853,157 A * 12/1974 Madaio ........................ 141/2

| 5,569,209 | A | 10/1996 | Roitman |
| 6,053,373 | A | 4/2000 | Sutton et al. |
| 6,073,759 | A | 6/2000 | Lamborne et al. |
| 6,494,314 | B1 | 12/2002 | Lamborne et al. |
| 6,599,280 | B1 * | 7/2003 | Pynson et al. ............... 604/403 |

FOREIGN PATENT DOCUMENTS

| EP | 1589962 | 11/2005 |
| WO | 8200780 | 3/1982 |
| WO | 8201176 | 4/1982 |
| WO | 0010423 | 3/2000 |
| WO | 0018661 | 4/2000 |
| WO | 0024649 | 5/2000 |
| WO | 2004069890 | 8/2004 |

OTHER PUBLICATIONS

"ARCEOLE Webmail", DELPHI MEDICA SRL, Jul. 4, 2003, www.delphimedica.it.
kitGas® Product Brochure, Feb. 2000, CHAUVIN-OPSIA SA, LaBege Cedex, France, www.chauvingroup.com.

* cited by examiner

*Primary Examiner*—Kevin C Sirmons
*Assistant Examiner*—Catherine N Witczak
(74) *Attorney, Agent, or Firm*—Young & Thompson (57) ABSTRACT

A device and a procedure for the extemporaneous preparation of an individual quantity of sterile treatment fluid that may be compressible, in particular a treatment gas, the device comprising a rigid cartridge (3) with an outlet valve, an administration syringe (4) and a filtration-type connection/sterilization device (5, 6). The cartridge (3) simply contains an individual quantity of treatment fluid under pressure, and the cylinder of the syringe (4) is adapted to contain this individual quantity.

20 Claims, 3 Drawing Sheets

Fig 1

DEVICE AND PROCEDURE FOR THE EXTEMPORANEOUS PREPARATION OF AN INDIVIDUAL QUANTITY OF STERILE LIQUID

The present invention relates to a device and a procedure for the extemporaneous preparation of an individual quantity of sterile treatment fluid that may be compressible, in particular a treatment gas, for the purposes of administration to a patient (human or animal).

Certain therapeutic or surgical applications require the administration of a sterile and compressible fluid, so-called treatment fluid, in particular a gas, for example air or a fluorocarbon gas ($CF_4$, $C_2F_6$, $C_3F_8$, ...), $SF_6$, $N_2$, $CO_2$, ... For example, certain ophthalmological surgical procedures require the topical administration of such a sterile, perfectly neutral treatment gas to the ocular cavity.

The general problem that therefore arises in this context is to make available to the practitioner an individual quantity (that is to say intended for a single patient) of this fluid in a perfectly sterile state, and under appropriate conditions for the envisaged administration.

Up to now, in practice the individual quantities of treatment gas are prepared by filling an administration syringe from a large volume gas cylinder under high pressure and via a pressure reducing valve and a filtration-type sterilisation device. However, these large size cylinders and the gas that they contain cannot be sterilised or maintained in a sterile state under satisfactory conditions. The transfer of the syringe from the non-sterile filling point at the cylinder to the sterile point of use (for example a surgical unit) requires numerous manipulations and precautions, involves risks of contamination, and does not provide for an ad hoc "traceability" of each individual quantity of treatment fluid administration to each patient.

U.S. Pat. No. 3,853,157 describes an apparatus for filling syringes with a liquid composition from a rigid cartridge containing a volume of liquid corresponding to several individual doses, and provided with a manually operated push button valve. The valve may be of the metering type in order to facilitate the rapid filling of a large number of syringes. This device does not guarantee the sterility of the liquid composition introduced into the syringe, which may be contaminated, in particular by contact with the outlet orifice of the valve of the cartridge, and is liable to be infected. The device is not compatible with the distribution of a compressible composition (gaseous composition or one containing a gas) since it is extremely problematical, if not impossible, to gauge precisely the dosage of the volume introduced into the syringe by simply observing the displacement of the piston.

The object of the invention is thus to obviate these disadvantages by proposing a device that is simple and reliable in use that permits the extemporaneous preparation, at the point of use, of an individual quantity of sterile treatment fluid that may be compressible, avoiding any loss of fluid during the assembly and preparation—in particular totally hermetic during the filling of the syringe—and any risk of compromising asepsis, and may itself be completely sterilised—in particular with ethylene oxide—without any risk, in particular without any risk of mixing or reaction of the treatment fluid with ethylene oxide.

The invention proposes in particular such a device that can be used and that is also particularly suitable and advantageous in the case where the treatment fluid is compressible, that is to say consists of a gas or contains a gas.

The invention also proposes such a device that ensures the follow-up ("traceability") of the administered doses of fluid.

The invention also proposes such a device that is simple and inexpensive to produce and that includes only a relatively small number of parts.

To this end, the invention relates to a device for the extemporaneous preparation of an individual quantity of sterile treatment fluid that may be compressible, for the purposes of its administration to a patient, said device comprising:

- a syringe for administering a dose of treatment fluid, comprising a piston sliding in a cylinder provided with an open axial end, so-called distribution end,
- a reservoir containing a quantity of treatment fluid under pressure, formed by a rigid cartridge equipped with an outlet valve capable of being hermetically connected in fluid communication with the distribution end of the syringe, and capable of being opened in order to release the treatment fluid under pressure into the cylinder of the syringe, wherein:
- it comprises a connection/sterilisation device containing a filtration-type sterilisation device provided with a fluid inlet and a fluid outlet, and capable of sterilising the treatment fluid flowing between the inlet and the outlet, this connection/sterilisation device being capable of permitting the assembly and hermetic connection of the cartridge and syringe for the purposes of filling the syringe with the sterilisation device interposed between the cartridge and the syringe, so that the fluid outlet of the sterilisation device can deliver, into the syringe, sterile fluid leaving the cartridge,
- the reservoir contains a quantity of treatment fluid under pressure such that the total quantity of treatment fluid that can be released at atmospheric pressure by the cartridge during the opening of the valve corresponds to an individual quantity of treatment fluid that can be contained completely in the cylinder of the syringe.

In other words, the cylinder of the syringe is capable of containing all the amount of treatment fluid (individual quantity) that can be released by the cartridge at atmospheric pressure.

The fact of using a rigid cartridge means in particular that in practice a perfect sterilisation of the whole device can be achieved. In fact, such a rigid cartridge may in particular be made of a metallic material forming a perfect barrier to the sterilisation fluid such as ethylene oxide. In addition, such a rigid cartridge can contain the treatment fluid without any risk of contamination of the said treatment fluid.

Furthermore, by ensuring that the pressurised rigid cartridge contains only an individual quantity of treatment fluid, that is to say a dose intended for a single administration, the invention runs directly counter to the prior art, in which instead the aim is always to contain a maximum quantity of treatment fluid in a minimum volume. However, the invention facilitates the operation of filling the syringe, including in the case of a treatment gas, by avoiding at one and the same time the premature expulsion of the piston from the cylinder, the introduction of an insufficient quantity, and the use of a metering valve, which is generally ineffective or imprecise in the case of a gas, and is in any case extremely complicated. Thus, the filling of the syringe takes place automatically without the user having to carry out a visual check of the dosage of the quantity introduced into the syringe, including in the case where the treatment fluid is compressible. In practice it is sufficient to ensure that the maximum volume of the cylinder of the syringe (piston in the extreme position remote from the distribution end of the syringe) is greater than the individual quantity of treatment fluid intended for a single administration and that can be released by the cartridge, which may nevertheless itself be greater than or equal to the quantitative amount required for the treatment of the patient (the user (doctor) then being able easily to expel the surplus treatment fluid from the cylinder by depressing the piston before the administration).

Furthermore, since the device according to the invention is intended for a single use and is equipped with a sterilisation device involving filtration of the treatment fluid passing into the syringe, which is itself previously sterilised, the sterile state of the quantity of treatment fluid contained in the syringe is ensured. In particular the risks of contamination, especially as regards the outlet valve of the cartridge, by pathogenic microorganisms that could result from a multiple use of the same reservoir of fluid, are minimised. Furthermore, even if the external parts of the outlet valve were infected, the fluid is sterilised by the sterilisation device before entering the syringe. In addition, with individual quantity and single use cartridges it is possible to follow up the administered quantities of fluid ("traceability").

Advantageously and according to the invention, the outlet valve is of the type that is axially and elastically urged towards the exterior in the sealing position and can be forced axially towards the interior of the cartridge so it can be opened, and the connection/sterilisation device is capable of forming an axial assembly of the syringe, of this connection/sterilisation device and of the valve of the cartridge, and permits the filling of the syringe without loss of treatment fluid by simply bringing together axially the syringe and the cartridge. Consequently the manipulation of the device according to the invention is particularly simple and ergonomic, both as regards the assembly and the filling of the syringe. It requires only two bearing points (in contrast to the device of U.S. Pat. No. 3,853,157, which requires three bearing points).

Furthermore, advantageously and according to the invention, the connection/sterilisation device comprises a portion for connection to the valve of the cartridge, this connection portion and this valve being adapted so that:

in a first phase of bringing together in a relative axial manner the valve and cartridge, an hermetic connection may be formed between them without actuating the valve of the cartridge, which remains closed, in a second phase of bringing together in a relative axial manner the valve and cartridge subsequent to the first phase, the valve is open.

Such a device prevents in particular any risk of loss of fluid at the same time as the assembly and connection, since the valve remains completely closed so long as the connection is not completely hermetic.

Advantageously and according to the invention, the valve of the cartridge is a female valve provided with a distribution orifice, a peripheral gasket, and an actuating cavity capable of receiving one end of a bifunctional delivery tube for actuating the valve and for ejecting the treatment fluid, and the said connection portion of the connection/sterilisation device forms a bifunctional delivery tube compatible with the female valve of the cartridge. Such an embodiment is particularly simple and advantageous, inexpensive, convenient and reliable in use.

Advantageously and according to the invention, in the embodiment in which the valve is a female valve, the connection/sterilisation device comprises an upstream hermetic connection device having, on one side, the said bifunctional delivery tube compatible with the female valve of the cartridge and, on the other side, a connecting means compatible with the inlet of the filtration-type sterilisation device.

Advantageously and according to the invention, the said connecting means of the upstream hermetic connection device is a truncated conical connection device—in particular a standard device (NF EN 1615) of the Luer® type—for example female device, paired with a truncated conical connection device—in particular standard device of the Luer® type—for example male device, formed by the inlet of the filtration-type sterilisation device.

Advantageously and according to the invention, the outlet of the filtration-type sterilisation device is capable of being connected directly—without intermediate connecting means—to the axial end of the administration syringe.

Advantageously and according to the invention, the outlet of the filtration-type sterilisation device is a female truncated conical connection device—in particular a standard device of the Luer® type—paired with a male truncated conical connection device—in particular a standard device of the Luer® type—formed by the axial end of the administration syringe.

By way of variation it is however possible to provide a downstream connection device designed to be interposed between the filtration-type sterilisation device and the distribution end of the administration syringe. Such a downstream connection device may for example be provided with a stop valve enabling in particular any entry or exit of fluid from the syringe to be prevented during the insertion of the administration needle in the syringe.

Moreover, advantageously and according to the invention, the cartridge comprises a flexible internal pocket containing the said individual quantity of treatment fluid under pressure connected to the outlet valve and to the exterior of the pocket (but to the interior of the cartridge), and an amount of thrust gas (in the gaseous state) capable of pressurising the treatment fluid contained in the pocket. Advantageously and according to the invention, the thrust gas is of the same type as the treatment fluid, in particular is identical to the treatment fluid when the latter is a treatment gas. Thus, the thrust gas does not itself represent any risk of toxicity or contamination for the patient.

Advantageously and according to the invention, the pressure of the treatment fluid in the cartridge is slightly greater than atmospheric pressure, so as to prevent any accident or any premature loss during the assembly and the filling of the syringe. Advantageously and according to the invention, the amount of thrust gas is capable of maintaining in the pocket (when the latter contains the individual quantity of treatment fluid) an excess pressure (with respect to atmospheric pressure) of treatment fluid of less than 2000 hPa, in particular of the order of 600 to 1800 hPa. For this reason it is not necessary to provide a pressure reducing valve or a manometer, nor a stop valve for the filling of the syringe from the cartridge.

The initial pressure of the thrust gas in the gaseous state is capable of compressing any individual quantity of treatment fluid. In practice, this initial pressure may be adapted so that, at the end of distribution of the individual quantity of treatment fluid, the residual pressure of the thrust gas corresponds to atmospheric pressure or is slightly greater than atmospheric pressure, for example of the order of 1050 hPa. The corresponding slight excess pressure (of the order of 20 to 70 hPa) is found in practice to be generally sufficient to expel all the individual amount of treatment fluid contained in the pocket, in particular in the case of a treatment gas. This slight excess pressure (resulting from the use of a thrust gas in the gaseous state) for the expulsion of the treatment fluid is also important in choosing, dimensioning and ensuring the efficiency of the filtration-type sterilisation device. In fact, sterilisation filters cannot in general withstand large pressures such as those that would be imparted (typically 6 to 20 times atmospheric pressure) by the use of a liquefied thrust gas chosen from gases compatible with a sterilisation by ethylene oxide.

Furthermore, advantageously and according to the invention, the cartridge comprises a volume of treatment fluid between 10 ml and 100 ml, in particular of the order of 40 ml, less than the total capacity of the syringe.

In addition, advantageously and according to the invention, the cartridge comprises a cap for hermetically closing the orifice of the female valve capable of preventing any penetration of sterilisation fluid into the valve and the cartridge, and that can be broken by introduction of the bifunctional delivery tube into the orifice of the valve. This cap, which comprises for example a film of aluminium foil, prevents any contact of the treatment fluid and/or of the valve of the cartridge with the sterilisation fluid, particularly ethylene oxide, which is toxic.

Advantageously, the device according to the invention comprises in addition a sterile needle capable of being connected to the distribution end of the syringe for the administration of the treatment fluid to the patient; and a label, particularly in the form of a bracelet, intended to be associated with the patient and that can include information identifying the cartridge of treatment fluid used. This bracelet informs the caring staff that the patient has been treated with the treatment fluid, so that appropriate precautions may be adopted for the subsequent care and treatments. This is particularly advantageous and important in the case of a treatment gas.

The device according to the invention comprises in addition an external sterile packaging containing all the constituent elements of the device in the sterile state. It is thus presented in the form of a single sterile package ready for use at the point of administration.

Advantageously and according to the invention, the syringe and the sterilisation device are previously assembled in the sterile state in the packaging. In particular, the syringe and the connection/sterilisation device are previously assembled and are present in sterile and assembled form in the packaging. In this way it is ensured that the internal cavity of the syringe receiving the treatment fluid can never be contaminated, even on opening the packaging, by virtue of the sterilisation device, which prevents any penetration of pathogenic organisms into this cavity. Moreover, even if the outlet of the valve of the cartridge or the cap that it carries is infected, the treatment fluid penetrating into the syringe is sterilised.

The invention also provides a procedure for the extemporaneous preparation of an individual quantity of sterile treatment fluid that may be compressible, in particular a treatment gas, for the purposes of administration to a patient by means of a device according to the invention.

Advantageously and according to the invention, the syringe, the connection/sterilisation device and the valve of the cartridge are assembled axially so as to form between them a communication that is hermetically sealed with respect to the surroundings, following which the syringe and the cartridge are brought together axially so as to open the valve and introduce into the syringe a predetermined dose of sterile treatment fluid by equilibration of the pressures. The treatment fluid may then be used undiluted or diluted. In the latter case, if the treatment fluid is a treatment gas, the treatment fluid in the syringe is diluted by:
  depressing the piston in order to eject the surplus treatment fluid from the syringe,
  retracting the piston in order to introduce into the syringe an amount of atmospheric dilution air through the filtration-type sterilisation device.

Advantageously and according to the invention, since the syringe and sterilisation device, in particular the connection/sterilisation device, are assembled beforehand, the axial assembly is simply effected by joining the inlet of the sterilisation device, in particular the bifunctional delivery tube, to the valve of the cartridge.

Advantageously and according to the invention, the filtration-type sterilisation device is next disconnected (after preparation of the quantity of treatment fluid to be administered in the syringe) from the syringe, to which an administration needle is then connected. The syringe together with the needle may then be used to administer the treatment fluid to the patient.

The device and the procedure according to the invention are particularly simple, reliable, and ensure a high degree of security in use without any risk of leakage, accident or contamination, including the case of a compressible treatment fluid, for which hitherto there is no satisfactory solution (the problems solved by the present invention have moreover in this case never been raised). The device and procedure also ensure that the administered doses of fluid can be followed up ("traceability").

The invention thus relates to a device and a procedure characterised by a combination of all or parts of the characteristics mentioned hereinbefore or hereinafter.

Other aims, characteristics and advantages of the invention will appear on reading the following description of one of the embodiments given by way of non-limiting example, and with reference to the accompanying figures in which:

Figure 1:
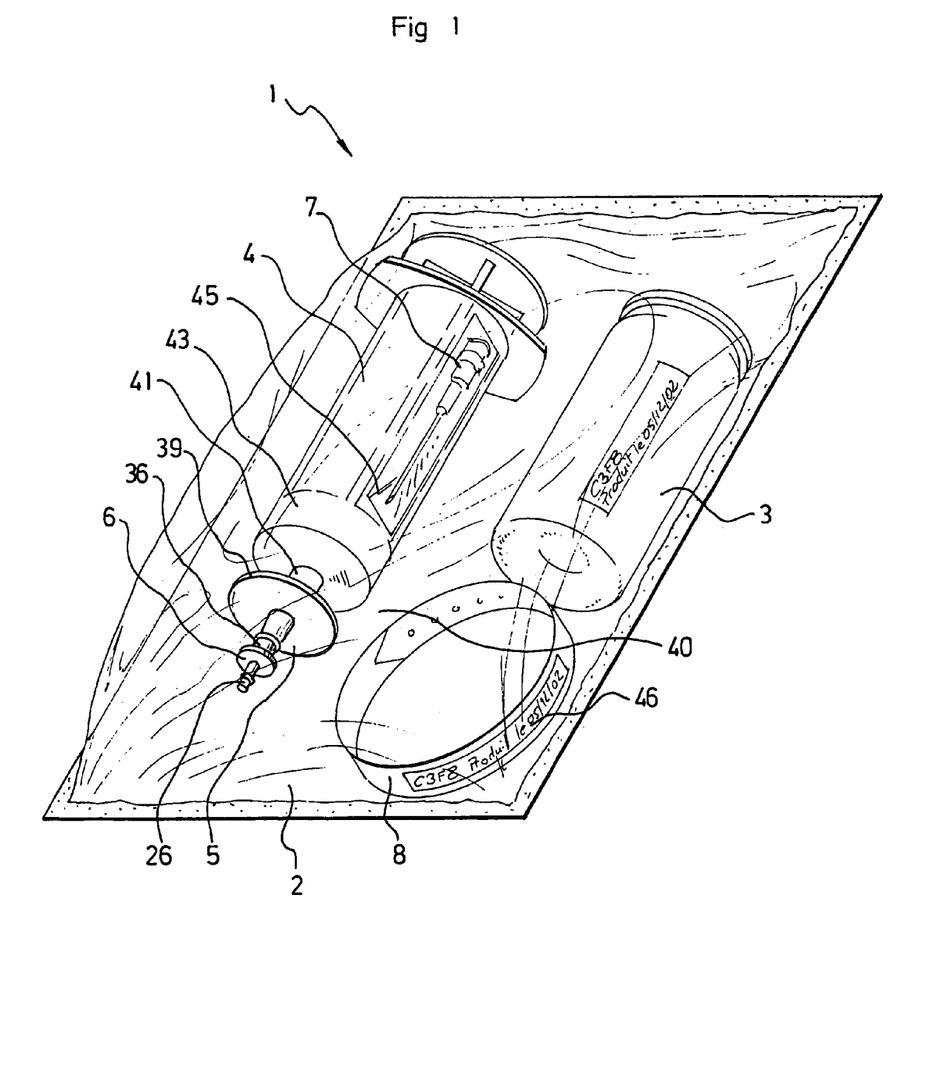
FIG. 1 is a perspective view illustrating an example of device according to the invention.

The device 1 according to the invention shown in FIG. 1 is in a sterile packaged state, ready for use, and comprises:
  an external sterile packaging 2 defining a sealed hermetic enclosure containing the various constituent elements of the device, namely:
  a rigid cartridge 3 acting as recipient containing an individual quantity of treatment fluid, in particular a treatment gas under pressure,
  an administration syringe 4,
  a filtration-type sterilisation device 5,
  an upstream hermetic connection device 6 intended to be interposed between the filtration-type sterilisation device 5 and the cartridge 3,
  an administration needle 7,
  a bracelet 8 intended to be worn by the patient.

All these constituent elements are of the single-use, disposable type.

Figure 2:
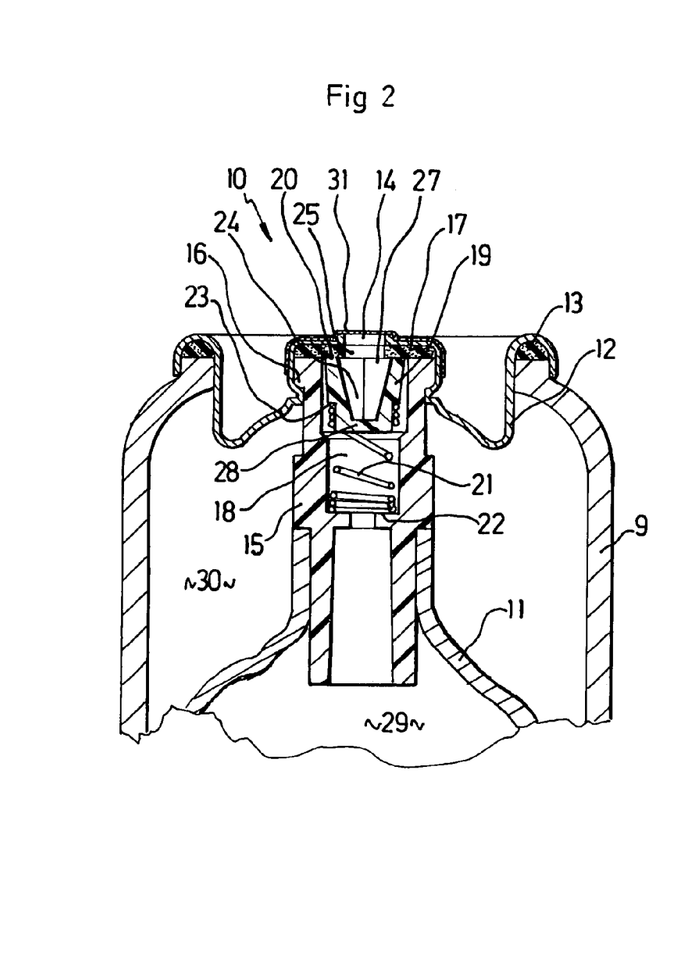
FIG. 2 is a sectional view of an embodiment of a treatment fluid cartridge valve of a device according to the invention before use.

The cartridge 3 comprises a rigid external metallic housing 9, in particular of aluminium or tin-plated iron, defining an end opening closed by an outlet valve 10 carrying a pocket 11, for example of the type marketed under the trade name EPSPRAY SYSTEM® by the company EP SPRAY SYSTEM SA (Neuchatel, Switzerland), extending into the interior of the housing 9 and with its internal enclosure in fluid communication with the valve 10.

The valve 10 comprises a rigid metallic closure wall 12 secured hermetically to the end of the housing 9 via a gasket 13 and having a central circular distribution orifice 14. A rigid sleeve 15 is secured underneath the orifice 14 by crimping this sleeve 15 by means of a tapering portion of the wall 12 clamped against an external crimping shoulder 16 of the sleeve 15. A peripheral gasket 17 is interposed between the end of the sleeve 15 and the portion of wall 12 defining the distribution orifice 14. This gasket 17 has a circular aperture 25 underneath the orifice 14.

The sleeve 15 defines at its upper end a bore 18 of larger diameter than the orifice 14 and than the internal diameter of the circular aperture 25 defined by the gasket 17, which is itself slightly smaller than that of the distribution orifice 14. This bore 18 contains a plug 19 having an upper sealing edge 20 in the form of a circular ring capable of coming into contact with the lower wall of the gasket 17 extending opposite the bore 18. The plug 19 is forced axially and elastically against the gasket 17 by means of a compression spring 21 arranged in the interior of the bore 18, and rests on one side against an internal collar 22 of the bore 18, and on the other side against a collar 23 of the external wall of the plug 19.

The external wall of the plug 19 has a radial size less than that of the bore 18 at the level of the sealing edge 20, with the result that there is a radial clearance between the sealing edge 20 and the bore 18. This clearance allows fluid to flow around the plug 19, and then between the gasket 17 and the sealing edge 20 when the plug 19 is urged towards the bottom against the spring 21.

The plug 19 also comprises an actuating cavity 24 in the form of a pyramidal shank adapted to receive the rotationally symmetrical axial end 34 of a rigid bifunctional delivery tube 26 for ejecting treatment fluid and actuating the valve 10. This delivery tube 26 is in the form of a rotationally symmetrical hollow tubular portion. The delivery tube is bifunctional in the sense that it can exercise a first function consisting in actuating the plug 19 and the valve 10 to open the latter, and a second function consisting in forming a passage for ejection of the treatment fluid from the valve 10 and the cartridge 3. The actuating cavity 24 has an upper end opening 27 whose radial dimensions are slightly greater than those of the aperture 25 of the gasket 17 and those of the distribution orifice 14. The actuating cavity 24 is closed at its lower end by a floor 28 of the plug 19 so that no treatment fluid can flow through the plug 19 when the latter is urged by the spring 21 with its sealing edge 20 against the gasket 17. The pyramidal cavity 24 has a polygonal, for example triangular, transverse cross-section so that a passage for treatment fluid is necessarily created between the internal wall of this cavity 24 and the rotationally symmetrical axial end 34 of the delivery tube 26 inserted into this cavity 24.

The pocket 11 is fixed hermetically, for example by adhesive bonding, to the external wall of the sleeve 15, whose bore 18 terminates in the interior of the pocket 11. This pocket 11 accordingly defines, on the one hand, an internal enclosure 29 that contains the treatment fluid and is in communication with the bore 18 up to the plug 19 and, on the other hand, between this pocket 11 and the external rigid wall of the housing 9 forms an intermediate enclosure 30 containing a suitable quantity of pressurised thrust gas in the gaseous state. This thrust gas is preferably a physiologically acceptable gas that is compatible with the treatment fluid and with the sterilisation process, in particular with ethylene oxide. In this way there is avoided, on the one hand, any complication in the case of accidental diffusion of the thrust gas into the treatment fluid and, on the other hand, any risk of accident during the course of the sterilisation stage with ethylene oxide.

The quantity of thrust gas contained in the intermediate enclosure 30 is capable of pressuring the treatment fluid in the enclosure 29 of the pocket 11 to an appropriate relative pressure. Advantageously and according to the invention, the quantity of thrust gas is capable of maintaining in the pocket 11 an excess pressure (with respect to atmospheric pressure) of treatment fluid of less than 2000 hPa, in particular of the order of 600 to 1800 hPa. This excess pressure is relatively small in magnitude but sufficient for the spontaneous filling of the syringe (the piston being driven by the pressure of the treatment fluid expelled from the valve), as explained hereinafter, without a pressure reducing valve or a stop valve. The pocket 11 in addition has a volume corresponding to that of the individual quantity of treatment fluid that is to be delivered by the cartridge 3, which is less than or equal to the maximum volume of the cylinder of the syringe 4. In practice, this volume of treatment fluid is typically between 10 ml and 100 ml, in particular of the order of 40 ml.

The invention is more particularly advantageously applicable to the case in which the treatment fluid is a treatment gas. This treatment gas may be chosen in particular from fluorocarbon gases ($CF_4$, $C_2F_6$, $C_3F_8$, ...), $SF_6$, $N_2$, $CO_2$, or air. Advantageously, in a device according to the invention the thrust gas is of the same type as the treatment fluid. In particular, the inventor has found that the majority of the treatment gases may in practice act as thrust gases. Such is particularly the case of fluorocarbon gases such as $CF_4$, $C_2F_6$, $C_3F_8$, etc.

The distribution orifice 14 of the sealing wall 12 of the valve 10 is advantageously hermetically closed before use by an hermetic closure cap 31 for this orifice 14. This cap 31 is hermetically adhesively bonded to the outside of the wall 12 and is capable of preventing any penetration of sterilisation fluid into the valve 10, in particular into the cavity 24 and into the bore 18, that is to say into the pocket 11. To this end, in the particular case where ethylene oxide is used as sterilisation gas, the cap 31 comprises at least one sheet of aluminium foil acting as an hermetic barrier to the ethylene oxide. This cap 31 is nevertheless sufficiently thin to allow it to be broken by the introduction of the bifunctional delivery tube 26 into the orifice 14 of the valve 10 for the purpose of filling a syringe. The cap 31 is of a non-flexible material so as to facilitate the rupture of this cap 31 by the delivery tube 26. It should however be sufficiently thick to offer a resistance requiring the exertion of an axial force above a threshold value in order to produce its rupture. In this way, any unintended rupture of the cap 31 and thus any premature actuation of the valve 10 is avoided.

Before use the cartridge 3 is as shown in FIG. 2 and thus contains an individual quantity of treatment fluid in the interior of the enclosure 29 of the pocket 11 under a relative pressure of the order of 600 to 1800 hPa, maintained by an identical relative pressure of thrust gas in the intermediate enclosure 30.

The upstream hermetic connection device 6 is a connection piece of synthetic material that can be sterilised, forming on one side the said bifunctional delivery tube 26 compatible with the female valve 10 of the cartridge 3, and on the other side forming a truncated conical connection 36, in particular a standard connection of the Luer® type, compatible with the fluid inlet 33 of the filtration-type sterilisation device 5. This connection piece 6 is hollow so as to form an axial passage for fluid through the delivery tube 26 and over its whole length.

Figure 3:
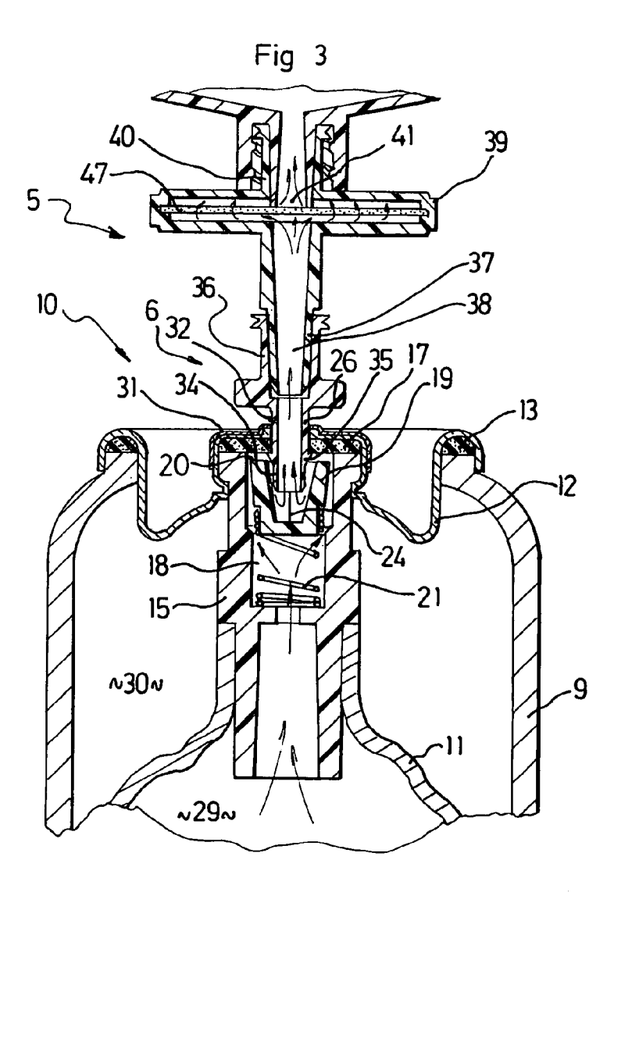
FIG. 3 is a similar view to FIG. 2 showing the valve during the filling of the syringe.

The bifunctional delivery tube 26 formed by this connection piece 6 should have dimensions compatible with those of the valve 10, that is to say with those of the distribution orifice 14 of the aperture 25, gasket 17 and actuating cavity 24 of the plug 19. It should be sufficiently rigid to permit the cap 31 to be broken and to force the plug 19 axially against the spring 21.

As can be seen in FIG. 3, the delivery tube 26 has a rotationally cylindrical external wall 32 of diameter slightly greater than that of the circular aperture 25 of the gasket 17, with the result that when this delivery tube 26 is introduced into the orifice 14 the gasket 17 comes into contact with a portion of this external wall 32, thereby ensuring it is fluid-tight with respect to the treatment fluid, in particular the treatment gas. The axial end 34 of the delivery tube 26 is preferably chamfered to facilitate the rupture of the cap 31 and may have a diameter slightly less than the external wall portion 32 coming into contact with the gasket 17. The external wall 32 of the delivery tube 26 may in addition comprise a section of increased thickness 35 between the axial end 34 and the cylindrical portion of this wall 32 coming into contact with the gasket 17. This section of increased thickness 35 preferably has a truncated conical shape as shown, narrowing towards the axial end 34, and has a non-return (reverse-lock) connecting collar with the external wall 32, so that it can be forcibly introduced by elastic deformation through the orifice 14 and the gasket 17, thereby subsequently preventing any premature axial disconnection of the delivery tube 26 outside the gasket 17 and the distribution orifice 14. The non-return collar may be in the form of a radial ring. The section of increased thickness 35 has an external diameter sufficiently large to effect an hermetic contact with the gasket 17 as soon as it comes into contact with this gasket 17. After the section of increased thickness 35 passes beyond the gasket 17, the external wall 32 ensures the maintenance of fluid tightness with respect to the treatment fluid.

In one embodiment the axial end 34 of the delivery tube 26 may itself also ensure a fluid tightness with the gasket 17.

In another embodiment the axial end 34 has a diameter smaller than the gasket 17, so that the fluid tightness is achieved only from the time when the section of increased thickness 35 comes into contact with the gasket 17. This dimensioning nevertheless has the advantage of facilitating the rupture of the cap 31, and the introduction and initial centering of the delivery tube 26 in the orifice 14 and the cavity 24.

In this second embodiment, the axial length of the axial end 34 of the delivery tube 26 is adapted (sufficiently weak) so that hermetic contact can be established between the section of increased thickness 35 or the external wall 32 of the delivery tube 26 and the gasket 17 during a first axial bringing together and introduction into the orifice 14, without this end 34 coming into contact with the wall of the actuating cavity 24, that is to say without opening of the valve 10.

However, the total axial length of the delivery tube 26, and in particular of the external wall 32, is adapted so that, in a second axial bringing together beyond the said first bringing together (the liquid tightness then being established), the end 34 of the delivery tube 26 comes into contact with the wall of the actuating cavity 24 in order to displace the latter and open the valve 10.

It should be noted that the presence of the cap 31 also has the effect of obliging the user to exert an axial force that is well aligned with the axis of the valve 10 and is sufficiently large so that the manoeuvre involving the introduction of the delivery tube 26 into the valve 10 up to its actuation proceeds correctly, virtually instantaneously and without any risk of leakage.

The axial end 34 then penetrates the actuating cavity 24 and enables the plug 19 to move axially towards the interior until the sealing edge 20 of the plug 19 is disengaged from the gasket 17. The shapes of the axial end 34 of the delivery tube 26 and of the fluid tightness cavity 24 are also adapted so that it is possible for treatment fluid to flow between the chamfered outer edge of the axial end 34 and the floor 28 of the cavity 24. Consequently, as can be seen in FIG. 3, as soon as the delivery tube 26 is introduced into the interior of the valve 10 and the plug 19 is pushed back axially, the treatment fluid in the pocket 11 can circulate around the plug 19 in the bore 18, between the gasket 17 and the sealing edge 20, between the cavity 24 and the axial end 34, and can then penetrate the interior of the delivery tube 26 so as subsequently to flow axially in the connecting piece 6 to the exterior of the cartridge 3.

The outlet valve 10 that is thereby formed is thus a valve that is urged axially elastically towards the exterior in the sealing position by the spring 21, and may be forced manually axially towards the interior so it can open in order to release the treatment fluid, and this by virtue of the bifunctional delivery tube 26 for ejecting the treatment fluid and actuating the valve 10.

The filtration-type sterilisation device 5 is for example a device as marketed by the MILLIPORE Company (Billerica, Mass., USA), under the name MILLEX®. Such a device 5 comprises a rigid hermetically sealed housing 39 of PVC containing a filter 47, in particular a microfilter, formed by a membrane whose pores have a size of the order of 0.2 μm, capable of retaining pathogenic microorganisms. This housing 39 has a fluid inlet 38 with a truncated conical connection 37 and a fluid outlet 40. The fluid outlet 40 forms a truncated conical connection compatible with its direct joining to the axial end 41 of the syringe 4. Preferably the fluid outlet 40 defines a female truncated conical connection with a standard screw-type locking, in particular of the "Luer-Lok®" type.

The upstream hermetic connecting piece 6 comprises, in contrast to the bifunctional delivery tube 26, a truncated conical connection 36 paired with the truncated conical connection 37 of the fluid inlet 38 of the filtration-type sterilisation device 5. Preferably these truncated conical connections 36, 37 comply with the standards currently in force, and in particular are of the Luer® type. Thus, in the case where the fluid inlet 38 of the filtration-type sterilisation device 5 is of the male connection type, the connecting piece 6 comprises a matching female truncated conical connection 36. Such is the case in the embodiment that is illustrated. It is understood of course that the filtration-type sterilisation device 5 may be provided with a fluid inlet 38 having a female truncated conical connection, in which case the connecting piece 6 then comprises a matching male truncated conical connection. The truncated conical connection 36 of the connecting piece 6 and the truncated conical connection 37 of the fluid inlet 38 of the filtration-type sterilisation device 5 may either be of the screw-type locking kind (in particular of the so-called Luer-Lok® type), or alternatively of the screwless type, the hermetic connection between them being achieved by simple relative sleeve-type engagement.

The administration syringe 4 is a standard disposable syringe with a volume between 10 ml and 100 ml, for example 50 ml. This syringe 4 comprises a piston 42 and a syringe body 43 defining a cylinder 44 in which the piston 42 may freely slide. The cylinder 44 terminates in the open axial end, so-called distribution end 41, of the body of the syringe 43. In the example illustrated this axial end 41 forms a standard screw-type male truncated conical connection of the "Luer-Lok®" type. This distribution end 41 is capable of being able to receive the needle 7, which is itself provided with a standard screw-type female truncated conical connection, in the conventional way. The needle 7 is itself packaged in a closed pocket 45 and may be inserted in the interior of the syringe body 43 into a groove in the manipulating rod of the piston 42, as shown in FIG. 1. The maximum volume of the cavity of the syringe 4 defined between the distribution end 41 and the piston 42 in the extreme position remote from the distribution end 41 is greater than or equal to the individual amount of treatment fluid that can be released from the cartridge 3 when the valve 10 is opened. The cartridge 3 contains in effect exactly a quantity of treatment fluid corresponding to an individual quantity intended for a single administration, and the cylinder of the syringe may contain all this individual quantity of treatment fluid. In a device according to the invention, the volume of treatment fluid contained in the cartridge 3 and that can be released by the latter for a single administration is thus predefined during manufacture. Accordingly, no dosage procedure has to be carried out by the user during the filling of the syringe.

The bracelet 8 is adapted so that it can be placed around the wrist of the treated patient, and this for a double purpose. First of all this bracelet 8 enables the caring staff to know immediately that the patient has undergone a treatment involving administration of fluid, in particular gas. The caring staff can thus avoid subsequent errors regarding care and adopt the necessary safety precautions for the patient thus treated. In fact, for example, certain therapeutic precautions should be taken with patients who have undergone treatment involving administration of gas so as to prevent any accident. In addition, the bracelet 8 may be provided with a label 46 containing information identifying the treatment fluid cartridge 3 used, and identical to the information on this cartridge 3. Other similar labels may also be envisaged for use in connection with the patient's medical records. In this way a perfect "traceability" of the treatment fluid is ensured.

An example of the procedure according to the invention for the use of the device according to the invention is illustrated in FIGS. 4 to 8 respectively. First of all, the external envelope 2 is opened after having checked that the sterilisation conditions have been suitably maintained (the external envelope 2 may be provided in a conventional manner with coloured indicators as a guarantee of sterility). The valve 10 of the cartridge 3 is then axially assembled with the syringe 4 previously provided with the filtration-type sterilisation device 5 and with the upstream hermetic connecting device 6, so as to produce a connection between them that is hermetically sealed with respect to the surroundings.

Figure 4:
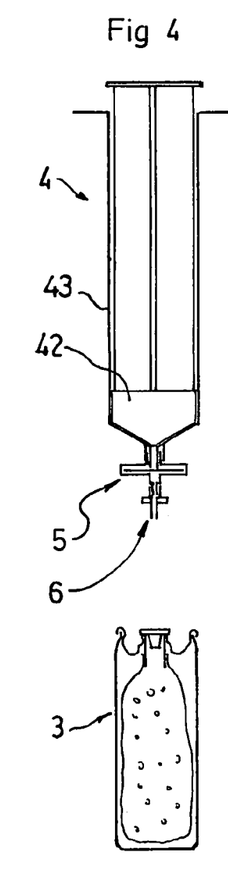
FIGS. 4 to 8 are sectional schematic views showing respectively different stages of a procedure according to the invention.

It should be noted that the syringe 4 and the sterilisation device 5, and preferably also the upstream hermetic connection device 6, are assembled together beforehand before being packaged in the envelope 2 and sterilised with ethylene oxide according to the invention. Accordingly, in order to effect the said hermetic communication it is sufficient to join the upstream hermetic connecting device 6 (already integral with the device 5 and the syringe 4) and the valve 10 of the cartridge 3. The prior assembly of the syringe 4 and of the sterilisation device 5 thus prevents any contact of the internal cavity of the syringe 4 with the surrounding air. This ensures that the contents of this cavity are always perfectly sterile.

Figure 5:
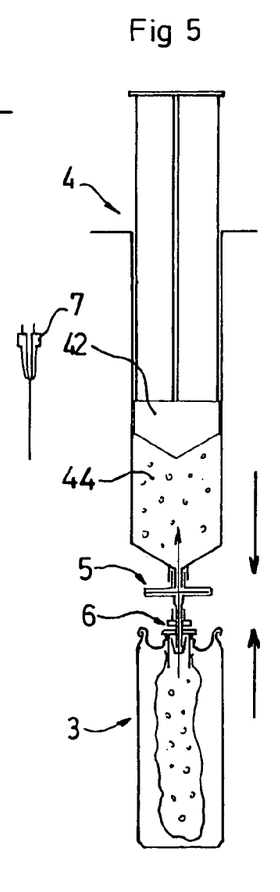

The syringe 4 and the cartridge 3 are then brought together axially so as to open the valve 10 and release the treatment fluid from the cartridge 3, which flows into the syringe 4 whose piston 42 is forced spontaneously to the exterior of the syringe body 43 by the pressure of treatment fluid thus introduced into the interior of the cylinder 44. The introduction of the individual quantity of treatment fluid into the syringe 4 thus takes place by equilibration of the pressures as soon as the syringe 4 and the cartridge 3 are brought together. The treatment fluid passing into the sterilisation device 5 is sterilised as it is being introduced into the cavity of the syringe 4.

Figure 6:
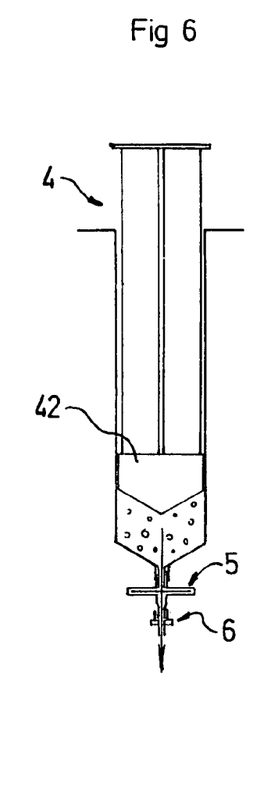

The cartridge 3 is then disconnected from the syringe 4. Preferably the connecting device 6 is disconnected from the valve 10 of the cartridge 3, for example by performing successive alternating angular movements while exerting an axial tractive force, so as to reveal the delivery tube 26 (and the section of increased thickness 35) in the orifice 14. The presence of the delivery tube 26, which is not compatible with the needle 7, prevents any subsequent accidental installation of this needle 7 before the separation of the filtration-type sterilisation device 5 from the syringe 4.

Figure 7:
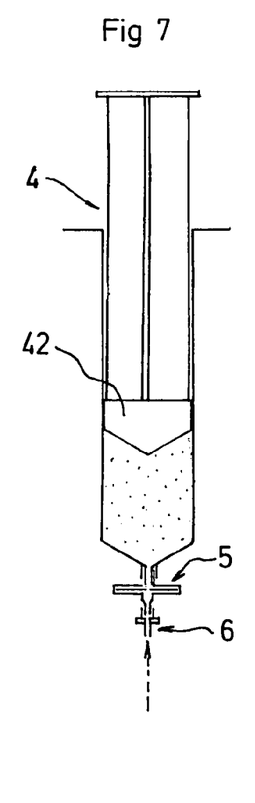
Figure 8:
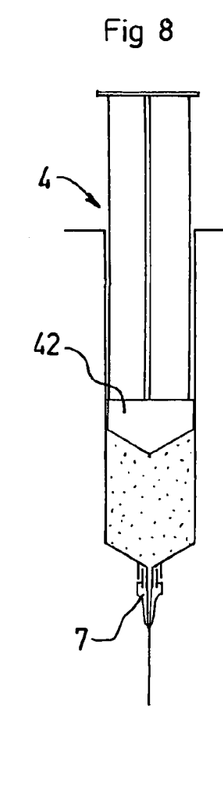

In the case where the treatment fluid is a gas, the said gas may then if necessary be diluted with atmospheric air by expelling the surplus of gas from the cylinder 44 and aspirating into the interior of the cylinder 44 a quantity of atmospheric dilution air through the filtration-type sterilisation device 5, which thus also sterilised this dilution air. These two stages corresponding to the dilution are not necessary, in particular in the case where the treatment fluid is used in the pure state. The filtration-type sterilisation device 5 is then disconnected from the syringe 4 and the needle 7 is rapidly inserted in the axial end 41 of the syringe. The resultant syringe shown in FIG. 8 is ready for use for administering treatment fluid to the patient.

It should be noted that, after the stage involving the filling of the cylinder of the syringe 4, it still remains possible to reinject part of the treatment fluid into the cartridge 3 by actuating the piston 42 via the hermetic communication that is thus effected. When doing this, the truncated conical section of increased thickness 35 of the delivery tube 26 prevents any premature disconnection of the cartridge 3 with respect to the connecting device 6. It is also possible to reinject into the cartridge 3 all the treatment fluid and to repeat the filling operation in the case where the latter might not have been carried out correctly.

The arrangement of the device according to the invention after packaging may be sterilised with ethylene oxide in a conventional way, at low cost and with a high degree of reliability. The presence of the cap 31 prevents any penetration of ethylene oxide into the interior of the valve 10 and contact with the treatment fluid. The device 1 is then presented all in one piece as a sterile ready-for-use packaged arrangement.

The invention may also be the subject of numerous modifications with respect to the embodiment described above and shown in the figures. For example, the cartridge 3 may contain only a treatment gas under pressure (without separating pocket, such as a fluorocarbon gas, in particular selected from $CF_4$, $C_2F_6$, $C_3F_8$ or $SF_6$, $CO_2$, $N_2$ or air). The bifunctional delivery tube may be formed directly by the inlet of the filtration-type sterilisation device 5. The cap 31 may be formed so as to have a reinforcement for guiding the delivery tube with regard to the orifice 14. The various truncated conical connections may be replaced in whole or in part by any other suitable form of connection that is fluid-tight with respect to the treatment fluid (adhesive-bonded cylindrical assembly, joint-type assembly, etc.).

The invention claimed is:

1. A device for the extemporaneous preparation of an individual quantity of sterile treatment fluid that may be compressible, for the purposes of administration to a patient, comprising:

a syringe (4) for administering a dose of treatment fluid, comprising a piston (42) sliding in a cylinder (44) provided with an open distribution end (41);

a reservoir (3) containing a quantity of treatment fluid under pressure, formed by a rigid cartridge (3) equipped with an outlet valve (10) capable of being hermetically connected in fluid communication with the distribution end (41) of the syringe (4), and capable of being opened in order to release the treatment fluid under pressure into the cylinder of the syringe; and a connection/sterilisation device (5, 6) containing a filtration-type sterilisation device (5) provided with a fluid inlet (38) and a fluid outlet (40), and capable of sterilising the treatment fluid flowing between the inlet (38) and the outlet (40), this connection/sterilisation device (5, 6) being capable of permitting the assembly and hermetic connection of the cartridge (3) and syringe (4) for the purposes of filling the syringe (4), with the sterilisation device (5) interposed between the cartridge (3) and the syringe (4), so that the fluid outlet (40) of the sterilisation device (5) can deliver, into the syringe (4), sterile fluid leaving the cartridge (3), wherein the reservoir (3) contains a quantity of treatment fluid under pressure such that the total quantity of treatment fluid that can be released at atmospheric pressure by the cartridge (3) during the opening of the valve (10) corresponds to an individual quantity of treatment fluid that can be contained completely in the cylinder (44) of the syringe (4), wherein the outlet valve (10) is of the type that can be axially and elastically displaced towards the exterior in the sealing position and can be axially urged towards the interior in order to open the valve so as to release the treatment fluid, and wherein the connection/sterilisation device (5, 6) is capable of effecting an axial assembly of the syringe (4), this connection/sterilisation device (5,6), and the valve (10) of the cartridge, and of permitting the filling of the syringe (4) without loss of treatment fluid by simply axially bringing together the syringe (4) and the cartridge (3), and wherein the connection/sterilisation device (5, 6) comprises a connection portion (26) to the valve (10) of the cartridge (3), and wherein this connection portion (26) and this valve (10) are adapted so that:

in a first relative axial bringing together of the components, an hermetic connection may be formed between them without actuating the valve (10) of the cartridge (3), which remains closed, and in a second relative axial bringing together of the components subsequent to the first bringing together, the valve (10) is open.

2. A device as claimed in claim 1, wherein:

the valve (10) of the cartridge (3) is a female valve provided with a distribution orifice (14), a peripheral gasket (17), and an actuating cavity (24) capable of receiving an end (24) of a bifunctional delivery tube (26) for actuating the valve (10) and ejecting the treatment fluid, the said connecting portion (26) of the connection/sterilisation device (5, 6) forms a bifunctional delivery tube (26) compatible with the female valve (10) of the cartridge (3).

3. A device as claimed in claim 2, wherein the connection/sterilising device (5, 6) comprises an upstream hermetic connection device (6) having, on one side, the said bifunctional delivery tube (26) compatible with the female valve (10) of the cartridge (3) and, on the other side, a connection (36) compatible with the inlet (38) of the filtration-type sterilisation device (5).

4. A device as claimed in claim 3, wherein the said connection (36) of the upstream hermetic connection device (6) is a truncated conical connection paired with a truncated conical connection (37) formed by the inlet of the filtration-type sterilisation device (5).

5. A device as claimed in claim 2, wherein the cartridge (3) comprises a cap (31) for the hermetic closure of the orifice (14) of the female valve (10) adapted to prevent any penetration of sterilisation fluid into the valve (10) and the cartridge (3), and that can be broken by introduction of the bifunctional delivery tube (26) into the orifice (14) of the valve (10).

6. A device as claimed in claim 1, wherein the outlet (40) of the filtration-type sterilisation device (5) is capable of being able to be connected directly to the axial end (41) of the administration syringe (4).

7. A device as claimed in claim 1, wherein the outlet (40) of the filtration-type sterilisation device (5) is a female truncated conical connection paired with a male truncated conical connection formed by the axial end (1) of the administration syringe (4).

8. A device as claimed in claim 1, wherein the cartridge (3) comprises a flexible internal pocket (11) containing the said individual quantity of treatment fluid under pressure connected to the outlet valve (10) and to the exterior of the pocket (11), a quantity of thrust gas capable of pressurising the treatment fluid contained in the pocket (11).

9. A device as claimed in claim 8, wherein the thrust gas is a physiologically acceptable gas.

10. A device as claimed in claim 8, wherein the thrust gas is of the same type as the treatment fluid.

11. A device as claimed in claim 8, wherein the quantity of thrust gas is capable of maintaining in the pocket (11) an excess pressure of treatment fluid of less than 2000 hPa, in particular of the order of 600 to 1800 hPa.

12. A device as claimed in claim 1, wherein the treatment fluid is a treatment gas.

13. A device as claimed in claim 1, wherein the cartridge (3) comprises a volume of treatment fluid between 10 ml and 100 ml, in particular of the order of 40 ml.

14. A device as claimed in claim 1, further comprising a sterile needle (7) capable of being connected to the end (41) of the syringe (4) for the administration of the treatment fluid to the patient.

15. A device as claimed in claim 1, further comprising a label (46), in particular in the form of a bracelet (8), designed to be associated with the patient.

16. A device as claimed in claim 1, further comprising a sterile external packaging (2) containing all the constituent elements (3, 4, 5, 6, 7, 8) of the device in the sterile state, the whole device adapted to be sterilized with ethylene oxide after packaging.

17. A device as claimed in claim 16, wherein the syringe (4) and the sterilisation device (5) are assembled beforehand in the sterile state in the packaging (2).

18. A procedure for the extemporaneous preparation of an individual quantity of sterile treatment fluid that may be compressible, for the purposes of administration of the fluid to a patient, the procedure comprising the steps of:

with a device (1) for the extemporaneous preparation of an individual quantity of sterile treatment fluid that may be compressible, for the purposes of administration to a patient, comprising i) a syringe (4) for administering a dose of treatment fluid, comprising a piston (42) sliding in a cylinder (44) provided with an open distribution end (41), ii) a reservoir (3) containing a quantity of treatment fluid under pressure, formed by a rigid cartridge (3) equipped with an outlet valve (10) capable of being hermetically connected in fluid communication with the distribution end (41) of the syringe (4), and capable of being opened in order to release the treatment fluid under pressure into the cylinder of the syringe; and iii) a connection/sterilisation device (5, 6) containing a filtration-type sterilisation device (5) provided with a fluid inlet (38) and a fluid outlet (40), and capable of sterilising the treatment fluid flowing between the inlet (38) and the outlet (40), this connection/sterilisation device (5, 6) being capable of permitting the assembly and hermetic connection of the cartridge (3) and syringe (4) for the purposes of filling the syringe (4), with the sterilisation device (5) interposed between the cartridge (3) and the syringe (4), so that the fluid outlet (40) of the sterilisation device (5) can deliver, into the syringe (4), sterile fluid leaving the cartridge (3), wherein the reservoir (3) contains a quantity of treatment fluid under pressure such that the total quantity of treatment fluid that can be released at atmospheric pressure by the cartridge (3) during the opening of the valve (10) corresponds to an individual quantity of treatment fluid that can be contained completely in the cylinder (44) of the syringe (4), initially assembling the syringe (4) and the sterilisation device (5); and axially asemblying the sterilisation device to the valve (10) of the cartridge (3) by connecting the inlet of the sterilisation device to the valve (10) of the cartridge (3), wherein, the syringe (4), the connection/sterilisation device (5, 6), and the valve (10) of the cartridge (3) are axially assembled so as to form between them a communication that is hermetically sealed from the surroundings, and the syringe (4) and the cartridge (3) axially brought together so as to open the valve (10) and introduce into the syringe (4) a predetermined dose of sterile treatment fluid, by equilibration of the pressures.

19. A procedure as claimed in claim 18, wherein the treatment fluid is diluted in the syringe (4).

20. A procedure as claimed in claim 18, wherein the filtration-type sterilisation device (5) is next disconnected from the syringe (4), to which an administration needle (7) is then connected.

* * * * *

UNITED STATES PATENT AND TRADEMARK OFFICE
CERTIFICATE OF CORRECTION

PATENT NO. : 7,744,580 B2 Page 1 of 1
APPLICATION NO. : 10/771325
DATED : June 29, 2010
INVENTOR(S) : Gerard Reboul

It is certified that error appears in the above-identified patent and that said Letters Patent is hereby corrected as shown below:

On the title page, column 1 line 1 amend item (54) to read as follows:

--(54) DEVICE AND PROCEDURE FOR THE EXTEMPORANEOUS PREPARATION OF AN INDIVIDUAL QUANTITY OF STERILE FLUID--.

Signed and Sealed this

Thirty-first Day of August, 2010

David J. Kappos
*Director of the United States Patent and Trademark Office*